US012653609B2

(12) United States Patent
    Zhou et al.

(10) Patent No.: US 12,653,609 B2
(45) Date of Patent: Jun. 16, 2026

(54) ELECTRODE, ELECTROPHYSIOLOGICAL CATHETER, AND ABLATION SYSTEM

(71) Applicant: SHANGHAI ARTECHMED MEDICAL TECHNOLOGY CO., LTD., Shanghai (CN)

(72) Inventors: Lei Zhou, Shanghai (CN); Meijiao Zhu, Shanghai (CN); Shengfeng Shi, Shanghai (CN); Wei Xue, Shanghai (CN)

(73) Assignee: SHANGHAI ARTECHMED MEDICAL TECHNOLOGY CO., LTD., Shanghai (CN)

( * ) Notice: Subject to any disclaimer, the term of this patent is extended or adjusted under 35 U.S.C. 154(b) by 378 days.

(21) Appl. No.: 18/555,990

(22) PCT Filed: Nov. 9, 2021

(86) PCT No.: PCT/CN2021/129490
§ 371 (c)(1),
(2) Date: Oct. 18, 2023

(87) PCT Pub. No.: WO2022/222434
PCT Pub. Date: Oct. 27, 2022

(65) Prior Publication Data
US 2024/0382249 A1    Nov. 21, 2024

(30) Foreign Application Priority Data
Apr. 23, 2021    (CN) .......................... 202110442108.6

(51) Int. Cl.
*A61B 18/14*        (2006.01)
*A61B 18/00*        (2006.01)
(52) U.S. Cl.
CPC .. *A61B 18/1492* (2013.01); *A61B 2018/0016* (2013.01); *A61B 2018/00267* (2013.01);
(Continued)

(58) Field of Classification Search
CPC ..... A61B 18/1492; A61B 18/12; A61B 18/14; A61B 2018/0016; A61B 2018/00267;
(Continued)

(56) References Cited

U.S. PATENT DOCUMENTS 10,172,673 B2 *   1/2019   Viswanathan ......... A61N 1/056
10,702,178 B2 *   7/2020   Dahlen .................. A61B 5/287
(Continued)

FOREIGN PATENT DOCUMENTS

CN          103687538 A      3/2014
CN          105078571 A      11/2015
(Continued)

*Primary Examiner* — Beverly M Flanagan
(74) *Attorney, Agent, or Firm* — MUNCY, GEISSLER, OLDS & LOWE, P.C.

(57)        ABSTRACT

An electrode (100), an electrophysiology catheter (200) and an ablation system are disclosed. The electrode (100) is configured to be disposed at a distal end of a catheter (200) and includes a proximal electrode portion (110), a main electrode portion (120) and a distal electrode portion (130), which are sequentially joined together from a proximal end to a distal end of the electrode. The main electrode portion (120) includes a first section (121) and a second section (122), which are joined to each other along an axis of the catheter (200). At least one of the proximal electrode portion (110) and the distal electrode portion (130) is configured to be movably connected to the catheter (200). The main electrode portion (120) is configured to switch between a contracted configuration and a folded configuration along with relative movement of the proximal electrode portion (110) and the distal electrode portion (130) along the catheter (200). When the main electrode portion (120) is in the contracted configuration, the main electrode portion (120) expands outwards in the radial direction of the catheter (200), such that the first section (121) and the second section (122) are inclined relative to each other and staggered in the
(Continued)

transverse direction of the catheter (200). Configuring the main electrode portion (120) in this way in the folded configuration, instead of twisting the electrode (100) to stagger the sections, can avoid a reduced contact area, or even increase the contact area, between the main electrode portion (120) and a predetermined site. This can improve an electric field present around the predetermined site and enhance ablation performance.

20 Claims, 6 Drawing Sheets

(52) U.S. Cl.
CPC ............... *A61B 2018/00577* (2013.01); *A61B 2018/1465* (2013.01)

(58) Field of Classification Search
CPC .. A61B 2018/00577; A61B 2018/1465; A61B 2018/1405; A61B 2018/1435
USPC .......................................................... 606/41
See application file for complete search history.

(56) References Cited

U.S. PATENT DOCUMENTS

| | | | |
|---|---|---|---|
| 2003/0114846 A1 | 6/2003 | Fuimaono et al. | |
| 2010/0076426 A1 | 3/2010 | de la Rama et al. | |
| 2014/0031816 A1 | 1/2014 | Hu et al. | |
| 2015/0018818 A1* | 1/2015 | Willard | A61N 1/3606 |
| | | | 606/41 |
| 2015/0257825 A1* | 9/2015 | Kelly | A61N 7/02 |
| | | | 606/41 |
| 2017/0071543 A1 | 3/2017 | Basu et al. | |
| 2018/0085160 A1 | 3/2018 | Viswanathan et al. | |
| 2019/0110750 A1 | 4/2019 | Dahlen et al. | |

FOREIGN PATENT DOCUMENTS

| | | | |
|---|---|---|---|
| CN | 107468331 A | 12/2017 | |
| CN | 110662483 A | 1/2020 | |
| CN | 111374658 A | 7/2020 | |
| CN | 111772783 A | 10/2020 | |
| CN | 112451083 A | 3/2021 | |
| CN | 112545643 A | 3/2021 | |
| CN | 113100919 A | 7/2021 | |
| CN | 113274124 A | 8/2021 | |
| CN | 215273267 U | 12/2021 | |
| EP | 2759276 A1 | 7/2014 | |
| EP | 3178384 A1 | 6/2017 | |

* cited by examiner

100

122

121

100

ELECTRODE, ELECTROPHYSIOLOGICAL CATHETER, AND ABLATION SYSTEM

CROSS REFERENCE TO RELATED APPLICATIONS

This application is a U.S. National Stage of International Application No. PCT/CN2021/129490 filed on Nov. 9, 2021, for which priority is claimed under 35 U.S.C. § 120; and this application claims priority of Application No. CN 202110442108.6 filed in China on Apr. 23, 2021 under 35 U.S.C. § 119, the entire contents of all of which are hereby incorporated by reference.

TECHNICAL FIELD

The present invention relates to the field of medical devices and, in particular, to an electrode, an electrophysiology catheter and an ablation system.

BACKGROUND

In the field of electrophysiological therapies, electrophysiology catheters are common means for delivering energy required for tissue ablation. Specifically, an electrophysiology catheter includes a catheter and an electrode provided at a tip of the catheter. After the catheter tip is inserted to a target site in need of treatment, energy is supplied to the electrode from an energy supply platform and delivered thereby to the target site that is brought into close abutment with the electrode to accomplish ablation. Such energy is usually delivered via a pulsed electric field (PEF) for inducing irreversible electroporation, which is cellularly selective and can, in particular, effectively avoid damage to the esophagus or phrenic nerve during pulmonary isolation ablation.

Electrophysiology catheters commonly used for PEF ablation are the Farawave catheters from Farapulse, the Farawave catheters include a conventional electrode composed of electrode rings disposed on a polymeric tube. When inserted to a target site, the tip of a catheter can be twisted into a staggered electrode arrangement enabling maximum contact of the electrode with the target site (e.g., a pulmonary vein). However, the "rings on tube" construction of the conventional electrode has a large footprint and limited electrode density, which are unfavorable to an effective ablation depth that can be achieved by the catheter.

Electrophysiology mapping catheters are also often used in pulmonary isolation ablation, such as the IntellaMap Orion™ high-resolution mapping catheters available from Boston Scientific Corporation, which utilize an electrode arranged on a flexible circuit to achieve high-density electrophysiology mapping. However, due to poor twist resistance of the flexible circuit, the tip of such a catheter is not suitable to be twisted and hence fitted against a pulmonary vein as much as possible (i.e., maximum contact therewith is unachievable), leading to limited mapping accuracy. Moreover, electrodes used in these mapping catheters are thin-film electrodes formed using sputtering or electroplating, which are known to be less favorable in establishing effective contact with a target site.

SUMMARY OF THE INVENTION

The present invention provides an electrode, an electrophysiology catheter and an ablation system. One of its objectives is to address the problem of non-maximum contact with a target site and hence affected ablation performance in a twisted configuration associated with conventional electrodes. It is another object of the present invention to address the problem of limited electrode density and hence a suboptimal ablation depth in a twisted configuration associated with conventional electrodes.

To this end, in one aspect of the present invention, there is provided an electrode adapted to be disposed at a distal end of a catheter and used to transmit energy between a device and a predetermined site. The electrode includes a proximal electrode portion, a main electrode portion and a distal electrode portion, which are sequentially joined together from a proximal end to a distal end of the electrode. The main electrode portion includes a first section and a second section, which are joined to each other along an axis of the catheter. At least one of the proximal electrode portion and the distal electrode portion is adapted to be movably connected to the catheter.

The main electrode portion is configured to switch between a contracted configuration and a folded configuration along with relative movement of the proximal electrode portion and the distal electrode portion along the catheter. When the main electrode portion is in the contracted configuration, the main electrode portion inwardly abuts on the catheter along a radial direction of the catheter, when the main electrode portion is in the folded configuration, the main electrode portion expands outward along the radial direction of the catheter so that the first section and the second section are inclined relative to each other to form a staggered arrangement along a transverse direction of the catheter.

Optionally, the main electrode portion may further include a folding portion, the folding portion joined to both the first section and the second section, wherein when the main electrode portion is in the folded configuration, the first section and the second section are folded and staggered through the folding portion.

Optionally, the folding portion may define a groove, when the main electrode portion is in the folded configuration, the groove is configured to receive the first section or the second section.

Optionally, the main electrode portion may be configured to switch between the contracted configuration and an intermediate configuration and between the intermediate configuration and the folded configuration, wherein when the main electrode portion is in the intermediate configuration, a projection of the folding portion on the catheter is located between the proximal electrode portion and the distal electrode portion.

Optionally, when the main electrode portion is in the contracted configuration and/or the intermediate configuration, the first section and the second section are staggered along the transverse direction of the catheter.

Optionally, the electrode may further include a proximal mounting portion and a distal mounting portion, the proximal mounting portion and the distal mounting portion both parallel to the axis of the catheter, the proximal mounting portion configured to connect to the catheter through the proximal electrode portion, the distal mounting portion configured to connect to the catheter through the distal electrode portion.

Optionally, at least one of the first section and the second section may be curved or a polyline.

Optionally, the first section and the second section may be both curved or polylines, and wherein the first section and the second section are curved toward opposite directions along the transverse direction of the catheter.

Optionally, the electrode may include a base and a sub-electrode disposed on the base and provided on the first section and/or the second section.

Optionally, the electrode may include a plurality of sub-electrodes, wherein the plurality of sub-electrodes are disposed on the first section at intervals in an extending direction of the first section, and/or wherein the plurality of sub-electrodes are disposed on the second section at intervals in an extending direction of the second segment.

Optionally, at least some of the sub-electrodes may have different radial dimensions.

Optionally, any of the sub-electrodes closer to the middle of the first section may have a greater radial dimension than any of the sub-electrodes closer to either end of the first section. Alternatively or additionally, any of the sub-electrodes closer to the middle of the second section may have a greater radial dimension than any of the sub-electrodes closer to either end of the second section.

Optionally, the radial dimension of the sub-electrodes on the first section gradually may decrease from the middle of the first section to its opposing ends. Alternatively or additionally, the radial dimension of the sub-electrodes on the second section may gradually decrease from the middle of the second section to its opposing ends.

Optionally, the sub-electrode may be raised over a surface of the base and adapted to be brought into contact with the predetermined site.

Optionally, the electrode may further include a transmission line, to which the sub-electrodes are electrically connected, and which is provided with an insulating layer insulating the sub-electrodes from one another.

Optionally, the electrode may further include a transmission line, to which the sub-electrode is electrically connected, wherein the sub-electrode has a flange which is covered by a layer onto the transmission line, thereby limiting the sub-electrode in position on the transmission line.

Optionally, the base may be embedded therein with an elastic nickel alloy.

Optionally, the base may be strip-like, wherein some of the sub-electrodes are provided on the first section and the remaining sub-electrodes are on the second section so that the sub-electrodes on the first section and those on the second section are positioned on opposite sides of the base.

In another aspect of the present invention, there is also provided an electrophysiology catheter including a catheter and the electrode as defined above, wherein at least one of the proximal electrode portion and the distal electrode portion of the electrode is movably connected to the catheter, and the main electrode portion of the electrode is configured to switch between the contracted and folded configurations along with relative movement of the proximal electrode portion and the distal electrode portion along the catheter.

Optionally, the electrophysiology catheter may include a plurality of said electrodes which are arranged circumferentially around the catheter.

Optionally, the plurality of the electrodes may be uniformly arranged circumferentially around the catheter.

Optionally, each of the electrodes may include a plurality of sub-electrodes which are scattered in intervals along the axis of the catheter into a sub-electrode group so that when the main electrode portions of the electrodes are in the contracted configuration, the sub-electrode groups of each adjacent pair of the electrodes are staggered along the axis of the catheter.

Optionally, the catheter may include an outer tube and a support shaft movably inserted within the outer tube, wherein the proximal electrode portion(s) of the electrode(s) is/are provided on the outer tube, and the distal electrode portion(s) of the electrode(s) is/are provided on the support shaft.

In a further aspect of the present invention, there is also provided an ablation system including the electrophysiology catheter as defined above.

In summary, the present invention provides an electrode, which is adapted to be disposed at a distal end of a catheter and includes a proximal electrode portion, a main electrode portion and a distal electrode portion, which are sequentially joined together from a proximal end to a distal end of the electrode. The main electrode portion includes a first section and a second section, which are joined to each other in an axial direction of the catheter. At least one of the proximal electrode portion and the distal electrode portion is movably connected to the catheter, and the main electrode portion is configured to switch between a contracted configuration and a folded configuration along with relative movement of the proximal electrode portion and the distal electrode portion along the catheter. When in the contracted configuration, the main electrode portion fits at its inner side over the catheter radially with respect thereto. When in the folded configuration, the main electrode portion is radially expanded outward with respect to the catheter so that the first section and the second section are inclined relative to each other and staggered transversely with respect to the catheter. Inclining and staggering the first section and the second section relative to each other as a result of radial expansion of the main electrode portion, instead of by twisting the electrode, can avoid a reduced contact area, or even increase the contact area, between the main electrode portion and a predetermined site. This can improve an electric field present around the predetermined site and enhance ablation performance.

BRIEF DESCRIPTION OF THE DRAWINGS

Those of ordinary skill in the art would appreciate that the accompanying drawings are provided to facilitate a better understanding of the present invention and do not limit the scope thereof in any sense, in which.

100—electrode; 110—proximal electrode portion; 120— main electrode portion; 121—first section; 122—second section; 123—folding portion; 124—groove; 130—distal electrode portion; 140—proximal mounting portion; 150—distal mounting portion; 160—base; 170—sub-electrode; 180—transmission line; 190—insulating layer; 200—catheter; 210—outer tube; 220—support shaft.

DETAILED DESCRIPTION

Objectives, advantages and features of the present invention will become more apparent upon reading the following more detailed description of the present invention with reference to the accompanying drawings. Note that the figures are provided in a very simplified form not necessarily drawn to exact scale and for the only purpose of facilitating easy and clear description of the embodiments. In addition, the structures shown in the figures are usually part of actual structures. In particular, as the figures tend to have distinct emphases, they are often drawn to different scales.

As used herein, the singular forms "a", "an" and "the" include plural referents. As used herein, the term "or" is generally employed in the sense of "and/or", "several" of "at least one", and "at least two" of "two or more than two". Additionally, the use of the terms "first", "second" and "third" herein is intended for illustration only and is not to be construed as denoting or implying relative importance or as implicitly indicating the numerical number of the referenced item. Accordingly, defining an item with "first", "second" or "third" is an explicit or implicit indication of the presence of one or at least two of the items, unless the context clearly dictates otherwise.

As used herein, in context of the orientation of a medical device during its normal operation, the term "proximal end" usually refers to an end thereof closer to an operator, and the term "dital end" usually refers to its end that enters the body of a patient first.

The present invention provides an electrode, an electrophysiology catheter and an ablation system. One of its objectives is to address the problem of non-maximum contact with a target site and hence affected ablation performance in a twisted configuration associated with conventional electrodes. It is another objective of the present invention to address the problem of low electrode density and hence a suboptimal ablation depth in a twisted configuration associated with conventional electrodes.

Detailed description is set forth below with reference to the accompanying drawings.

Figure 1:
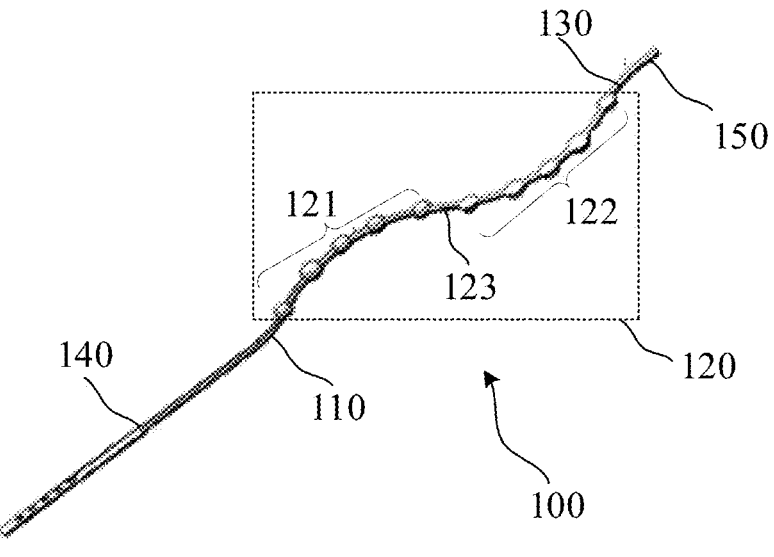
FIG. 1 is a schematic illustration of an electrode according to an embodiment of the present invention.
Figure 2:
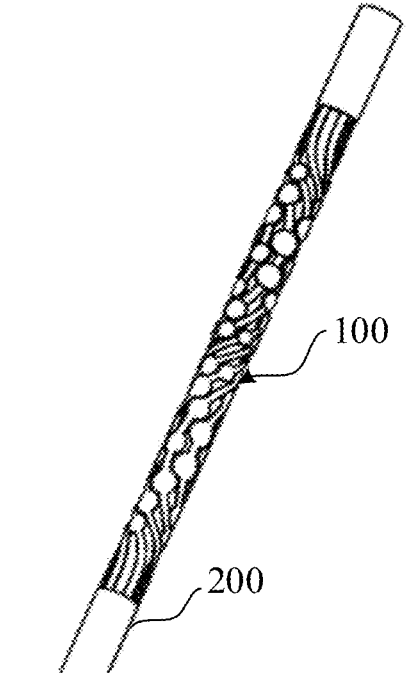
FIG. 2 is a schematic illustration of an electrode in a contracted configuration according to an embodiment of the present invention.
Figure 5:
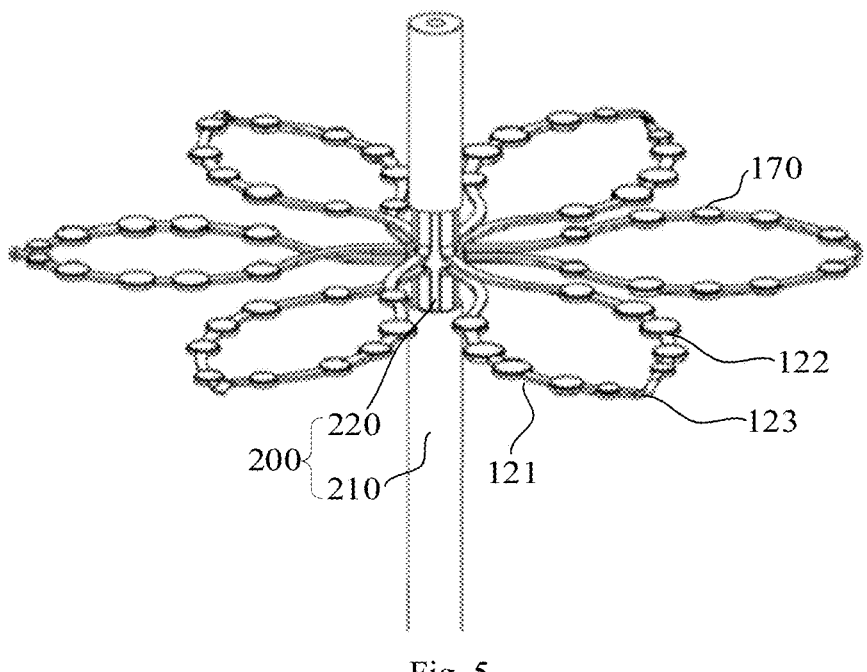
FIG. 5 is a schematic illustration of an electrode in a folded configuration according to an embodiment of the present invention.

Reference is now made to FIG. 1, in conjunction with FIG. 2. FIG. 1 is a schematic illustration of an electrode according to an embodiment of the present invention. FIG. 2 is a schematic illustration of the electrode in a contracted configuration according to an embodiment of the present invention. In this embodiment, the electrode 100 is configured to be disposed at a distal end of a catheter and to deliver energy (e.g., in the form of radio-frequency radiation, pulses or ultrasound waves) from a device (e.g., an energy supply platform) to a predetermined site (e.g., a pulmonary vein). The electrode 100 includes a proximal electrode portion 110, a main electrode portion 120 and a distal electrode portion 130, which are sequentially joined together from a proximal end to a distal end of the electrode. The main electrode portion 120 includes a first section 121 and a second section 122, which are joined to each other in an axial direction of the catheter 200. In this embodiment, the first section 121 is located closer to the proximal end, while the second section 122 is closer to the distal end. At least one of the proximal electrode portion 110 and the distal electrode portion 130 is movably connected to the catheter 200. The main electrode portion 120 is configured to switch between the contracted configuration and a folded configuration along with relative movement of the proximal electrode portion 110 and the distal electrode portion 130 in the axial direction of the catheter 200. With continued reference to FIG. 2, when in the contracted configuration, the main electrode portion 120 fits at the inner side of the catheter 200 along the radial direction of the catheter 200. Reference is now made to FIG. 5, FIG. 5 is a schematic illustration of the electrode in the folded configuration according to an embodiment of the present invention. When the main electrode portion 120 is in the folded configuration, the main electrode portion 120 is radially expanded outward with respect to the catheter 200 so that the first section 121 and the second section 122 are inclined relative to each other and staggered transversely with respect to the catheter 200. It would be appreciated that as a result of movement of the proximal electrode portion 110 and the distal electrode portion 130 toward each other, mutually facing ends of the first section 121 and the second section 122 radially move outward from the catheter 200 so that each of the first section 121 and the second section 122 is inclined at an angle with respect to the axial direction of the catheter 200. Here, the folded configuration refers to a configuration in which the main electrode portion 120 is folded as much as possible so that portions of the first section 121 and the second section 122 in proximity to the axis of the catheter come into substantial abutment with each other (possibly with a negligible gap between them). The inclination of the first section 121 and the second section 122 relative to each other means that the two are inclined toward each other and, more particularly, that the first section 121 and the second section 122 define an angle therebetween in a plane defining the transverse direction of the catheter 200. Notably, the first section 121 and the second section 122 do not coincide in the axial direction of the catheter 200. In this way, both the first section 121 and the second section 122 can come into abutment with the predetermined site, leading to a larger contact area. Here, the transverse direction of the catheter 200 refers to a direction substantially parallel to a cross-section of the catheter 200, and the axial direction of the catheter 200 is to be interpreted as a direction in which the catheter 200 substantially extends (the extension includes curved extension). With continued reference to FIG. 1, in conjunction with FIG. 2, optionally, the electrode 100 may further include a proximal mounting portion 140 and a distal mounting portion 150. The proximal electrode portion 110 may be connected to the catheter 200 through the proximal mounting portion 140, and the distal electrode portion 130 may be connected to the catheter 200 through the distal mounting portion 150. Preferably, both the proximal mounting portion 140 and the distal mounting portion 150 are parallel to the axial direction of the catheter 200.

Conventional structures for use in ablation (which are substantially geometrically to the electrode of this embodiment, i.e., being substantially linear, and referred to hereinafter as ablation electrodes) are composed of multiple electrode rings disposed side by side over a polymeric tube. After an ablation electrode is pushed and delivered to a target site by a catheter 200, a distal portion of the catheter 200 may be twisted to twist the ablation electrode into a staggered electrode arrangement. However, the "rings on tube" construction of the conventional ablation electrodes has a large footprint and hence limited electrode density. Moreover, due to poor twist resistance of the conventional construction, the ablation electrodes cannot be brought into maximum contact with a predetermined site in the twisted configuration. This can affect both an ablation depth and high-density mapping accuracy of the ablation electrodes. In contrast, according to the present embodiment, instead of twisting the electrode, the first section 121 and the second section 122 are staggered in the folded configuration along with relative movement of the proximal electrode portion 110 and the distal electrode portion 130. This allows for a greater contact area between the main electrode portion 120 and the predetermined site, which can improve an electric field present around the predetermined site and enhance ablation performance.

With continued reference to FIG. 5, the catheter 200 includes an outer tube 210 and a support shaft 220, the support shaft 220 is movably inserted in the outer tube 210 (thus, the catheter 200 can be considered as being telescopic), the support shaft 220 distally protrudes out of the outer tube 210. At least one of the proximal electrode portion 110 and the distal electrode portion 130 is movably connected to the catheter 200, and movement of the proximal electrode portion 110 and the distal electrode portion 130 along the catheter 200 relative to each other (leading to a varying distance therebetween) can be accomplished by any of the following designs:

(1) Both the proximal electrode portion 110 and the distal electrode portion 130 are movably disposed on the outer tube 210 or the support shaft 220 so that changes in the distance between the proximal electrode portion 110 and the distal electrode portion 130 can cause changes in the shape of the main electrode portion 120.

(2) One of the proximal electrode portion 110 and the distal electrode portion 130 is fixedly disposed on the catheter 200, and the other is movably disposed on the catheter 200. For instance, one of the proximal electrode portion 110 and the distal electrode portion 130 may be fixedly disposed on the support shaft 220, and the other may be movably disposed on the support shaft 220. Alternatively, one of the proximal electrode portion 110 and the distal electrode portion 130 may be fixedly disposed on the outer tube 210, and the other may be movably disposed on the outer tube 210.

(3) The outer tube 210 and support shaft 220 are locked against each other to prevent their relative sliding. The proximal electrode portion 110 is movably disposed on the outer tube 210, and/or the distal electrode portion 130 is movably disposed on the support shaft 220. This design also enables changes in the shape of the main electrode portion 120.

(4) The proximal electrode portion 110 is fixed to the outer tube 210, and the distal electrode portion 130 is fixed to the support shaft 220. The support shaft 220 can be moved in the outer tube 210 (the support shaft 220 is distally pushed and the support shaft 220 is proximally retracted) to cause relative movement of the proximal electrode portion 110 and the distal electrode portion 130.

In (1), (2) and (3), relative movement of the proximal electrode portion 110 and the distal electrode portion 130 may be guided by traction wire(s) tied to the proximal electrode portion 110 and/or distal electrode portion 130. It is to be noted that, in FIG. 2, the electrode 100 fits over the support shaft, and in order to schematically depict the catheter, "200" for the catheter is labeled on the outer tube. This should not be construed by a person of ordinary skill in the art as limiting the structure of the catheter in any sense.

The main electrode portion 120 may further include a folding portion 123, the folding portion 123 is joined to both the first section 121 and the second section 122, when the main electrode portion 120 is in the folded configuration, the first section 121 and the second section 122 are folded and arranged in a staggered manner through the folding portion 123. The provision of the folding portion 123 is advantageous because this can avoid a reduction in contact area for the first section 121 or the second section 122 in the folded configuration, maximize the staggered folding of the first section 121 or the second section 122, and reduce resistance that the first section 121 and the second section 122 encounter before the staggered folding is attained. Optionally, the folding portion 123 may be formed of an insulating material. Preferably, the folding portion 123 defines a groove 124, when the main electrode portion 120 is in the folded configuration, the groove 124 is configured for receiving the first section 121 or the second section 122. In this way, in this configuration of the main electrode portion 120, the first section 121 and the second section 122 will be substantially positioned in the same (curved) plane and therefore better contact of them with the predetermined site can be obtained.

Figure 6:
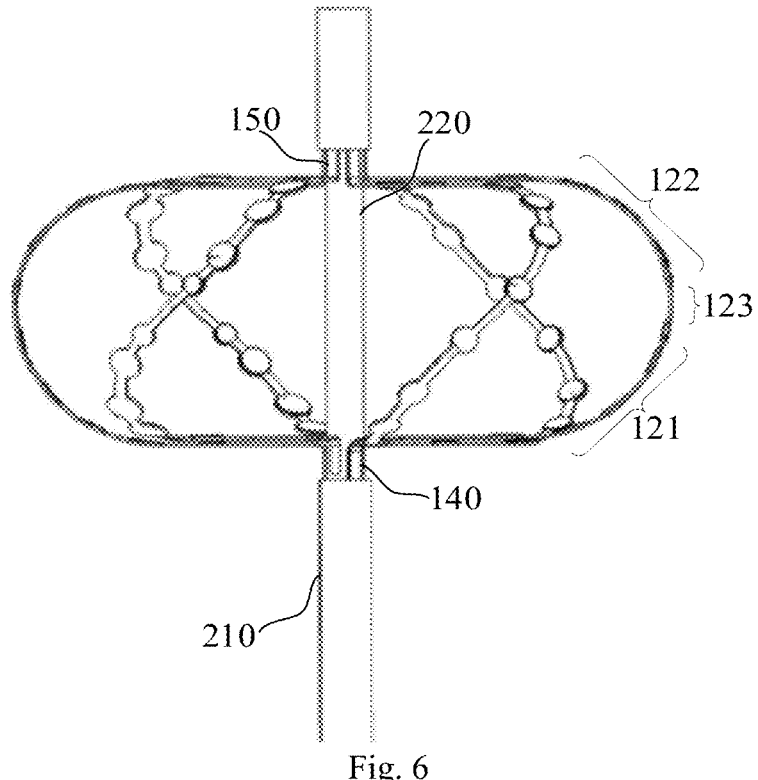
FIG. 6 is a schematic illustration of an electrode in an intermediate configuration according to an embodiment of the present invention electrode.

Reference is made to FIG. 6, FIG. 6 is a schematic depiction of the electrode in an intermediate configuration according to an embodiment of the present invention. In this embodiment, the main electrode portion 120 may assume the intermediate configuration. Specifically, the main electrode portion 120 may switch between the contracted configuration and the intermediate configuration and between the intermediate configuration and the folded configuration. When the main electrode portion 120 is in the intermediate configuration, a projection of the folding portion 123 on the catheter 200 (it is projected onto the catheter 200 along a radial direction of the catheter 200) is located between those of the proximal electrode portion 110 and the distal electrode portion 130. It would be appreciated that when in the intermediate configuration, the main electrode portion 120 defining a cross-sectionally semi-elliptical structure with the catheter 200. In fact, ablation treatment can be performed on the wall of a physiological lumen in the intermediate configuration of the main electrode portion 120.

Optionally, when the main electrode portion 120 is in the contracted configuration and/or the intermediate configuration, the first section 121 and the second section 122 may be staggered transversely with respect to the catheter 200. As noted above, the first section 121 and the second section 122 are staggered transversely with respect to the catheter 200 when the main electrode portion 120 is in the folded configuration. According to this embodiment, in the contracted, intermediate and folded configurations of the main electrode portion 120, the first section 121 and the second section 122 may assume any of the following arrangements:

(1) In each of the contracted, intermediate and folded configurations, the first section 121 and the second section 122 are staggered transversely with respect to the catheter 200, wherein the first section 121 and the second section 122 substantially fit over the catheter 200 (i.e., over an inner wall surface of the outer tube 210, or over an outer wall surface of the support shaft 220), and the main electrode portion 120 is substantially curled, when in the contracted configuration.

(2) The first section 121 and the second section 122 are not staggered (transversely with respect to the catheter 200) when in the contracted or intermediate configuration of the main electrode portion 120 (e.g., they may be positioned at the same axial point of the catheter 200). However, in the folded configuration, the first section 121 and the second section 122 are staggered (transversely with respect to the catheter 200).

(3) The first section 121 and the second section 122 are staggered (transversely with respect to the catheter 200) in one of the contracted and intermediate configurations of the main electrode portion 120, the first section 121 and the second section 122 are not staggered (transversely with respect to the catheter 200) in the other of the contracted and intermediate configurations of the main electrode portion 120. Moreover, in the folded configuration, the first section 121 and the second section 122 are staggered (transversely with respect to the catheter 200).

In this embodiment, the first section 121 and the second section 122 are staggered transversely with respect to catheter 200 in each of the above three configurations of the main electrode portion 120.

Figure 7:
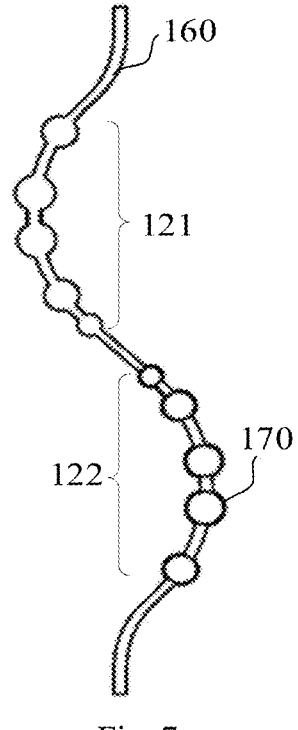
FIGS. 7 to 8 are schematic illustrations of an electrode according to a preferred embodiment of the present invention.
Figure 8:
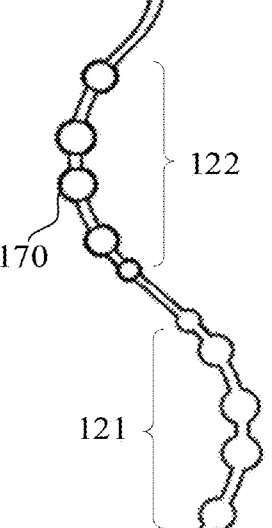

Preferably, with continued reference to FIG. 1, in conjunction with FIGS. 7 and 8, FIGS. 7 and 8 are schematic illustrations of the electrode according to a preferred embodiment of the present invention, at least one of the first section 121 and the second section 122 is curved, or is a polyline. This arrangement can reduce an overlap of the first section 121 and the second section 122 in the folded configuration of the main electrode portion 120 and thus enables a better arrangement thereof. Preferably, both the first section 121 and the second section 122 are curved or polylines, the first section 121 and the second section 122 curved towards opposite directions transversely with respect to the catheter 200. With this arrangement, the main electrode portion 120 is substantially S-shaped when the main electrode portion 120 is in the contracted configuration. In the folded configuration, a lower portion of the S-shaped curve may be folded upward and brought into abutment with the rest (upper portion) so that the main electrode portion 120 is substantially petal-like. In addition, when in the contracted configuration, proximal mounting portion 140 and the distal mounting portion 150 is substantially or almost collinear in order to facilitate assembly by a technician. Preferably, the centers of the proximal mounting portion 140, the distal mounting portion 150 and the folding portion 123 are located on the same axis (i.e., the axis of the catheter 200), with the first section 121 and the second section 122 being positioned on opposite sides of the axis. It would be appreciated that, as used herein, the term "polyline" refers to a line consisting of a number of segments, which are joined end-to-end along the axis of the catheter 200 so that any adjacent pair of them defines a negligible small angle (e.g., 5°). Thus, such a polyline can also be considered as being overall curved.

Figure 3:
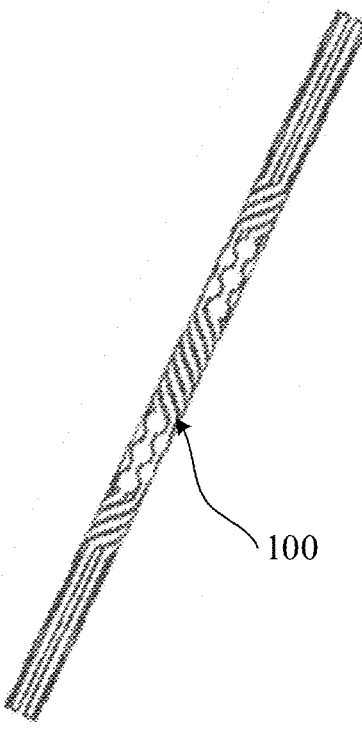
FIG. 3 is a schematic illustration of an electrode in a contracted configuration according to another embodiment of the present invention.
Figure 4:
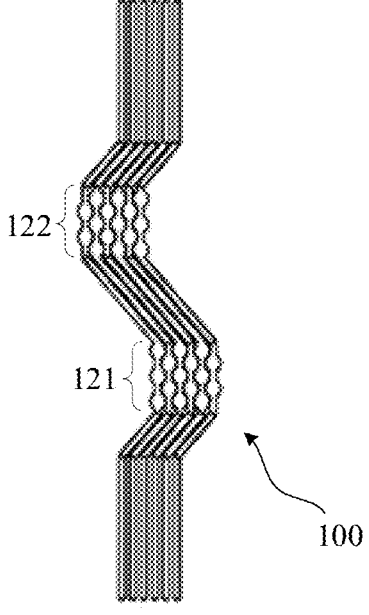
FIG. 4 is an unrolled view of the electrode of FIG. 3.
Figure 9:
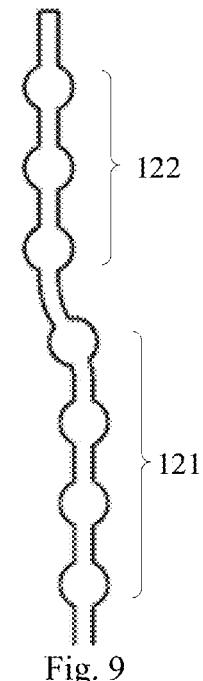
FIG. 9 is a schematic illustration of an electrode according to another embodiment of the present invention.

Reference is now made to FIGS. 3, 4 and 9. FIG. 3 is a schematic illustration of the electrode in the contracted configuration according to another embodiment of the present invention. FIG. 4 is an unrolled view of the electrode of FIG. 3. FIG. 9 is a schematic illustration of the electrode according to another embodiment of the present invention. Of course, in some alternative embodiments, the first section 121 and the second section 122 may be straight lines extending substantially parallel to the axial direction of the catheter 200 and connected with a curved (FIG. 9) or oblique (FIG. 4) transition. When the main electrode portion 120 is in the folded configuration, the first section 121 and the second section 122 are substantially parallel to each other. It is to be noted that as FIG. 3 focuses on the illustration of the electrode being contracted over the catheter, only the electrode is labeled while the catheter is not.

Figure 10:
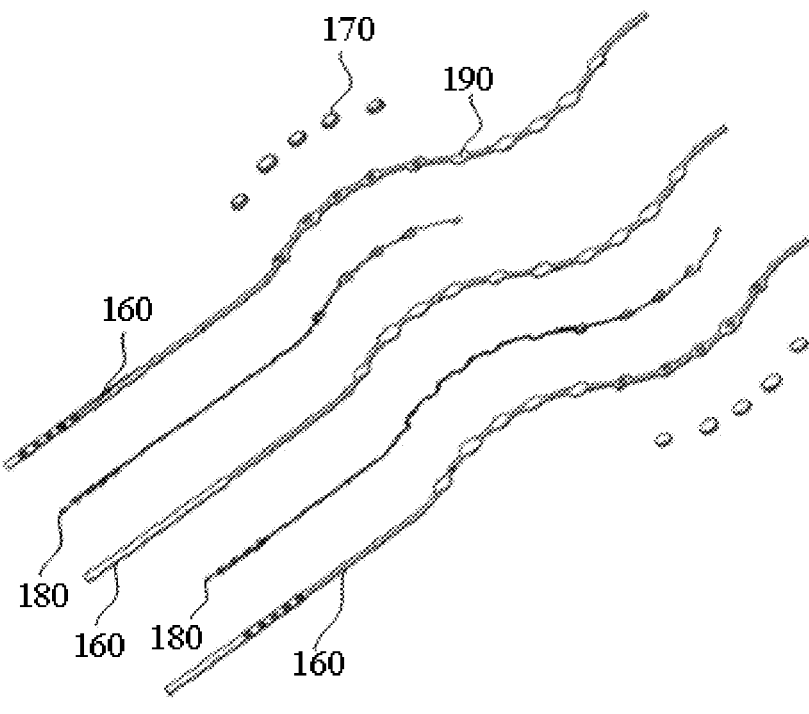
FIG. 10 is a schematic illustration of a sub-electrode, a base and a transmission line according to an embodiment of the present invention.
Figure 11:
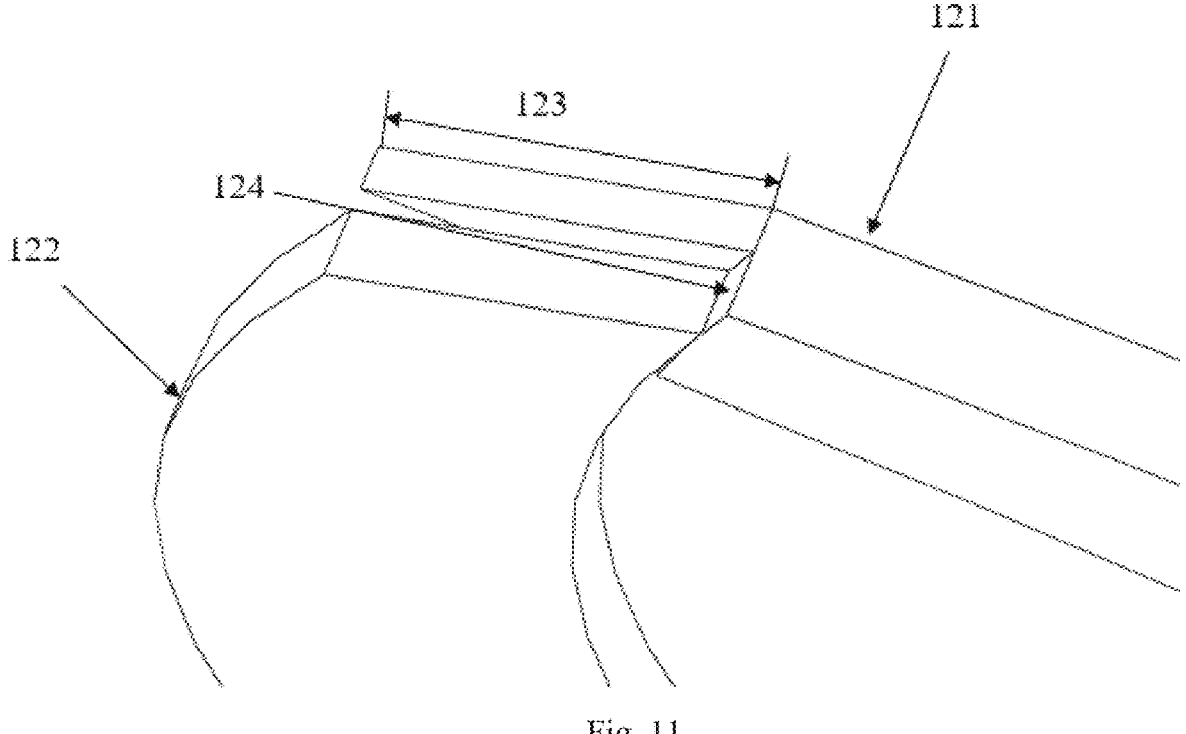
FIG. 11 is a schematic illustration of a folding portion of an electrode according to an embodiment of the present invention, wherein the electrode is in a folded configuration. In these Figures.

Reference is additionally made to FIG. 10, FIG. 10 is a schematic illustration of a sub-electrode, a base and a transmission line according to an embodiment of the present invention. The electrode 100 includes the base 160 and the sub-electrode 170. The first section 121 and the second section 122 are both provided on the base 160, and the sub-electrode 170 is disposed on the first section 121 and/or the second section 122. The sub-electrodes 170 are configured to transmit ablation energy to the predetermined site. The sub-electrode 170 may be made of platinum or gold. For a small site to be ablated, for example, at the orifice of a pulmonary vein, the sub-electrode 170 may be designed with a relatively large radial dimension, which allows satisfactory ablation while resulting in material savings. The present invention is not limited to any particular shape (or more precisely, cross-sectional shape) of the sub-electrode 170, and it may have a circular, elliptic, polygonal, irregular planar or another shape. Here, the radial dimension may be interpreted as a maximum radial dimension of the sub-electrode 170 measured between its opposing edges. If the sub-electrode 170 has a circular cross-sectional shape, the radial dimension may refer to its diameter. It is to be noted that the sub-electrode 170 is preferred to be shaped as a sheet, instead of as a ring as is conventional. The sub-electrode 170 may be substantially dome-shaped or screw-shaped and embedded in the base 160. The sub-electrode 170 can be brought into contact with the predetermined site at its surface. Compared with conventional electrode rings, a larger contact area can be achieved with the sub-electrode 170. Preferably, the base 160 is made of an insulating material such as a liquid-crystal polymer (LCP), polyimide (PI) or polydimethylsiloxane (PDMS). More preferably, in order to enhance support that the electrode can provide, the base 160 may be embedded therein with an elastic nickel alloy. Properties of such nickel-titanium alloys will not be detailed herein, because they are well known to those of ordinary skill in the art. It would be appreciated that the present embodiment is not limited to enhancing support provided by the electrode 100 with a nickel-titanium alloy, and any material that allows the electrode 100 to provide enhanced support and has no side effects on patients can be suitable embedded in the base 160.

Preferably, the electrode includes a plurality of sub-electrodes 170. With combined reference to FIGS. 7 and 8, the sub-electrodes 170 may be disposed at intervals on the first section 121 in the direction of extension of the first section 121 and/or the sub-electrodes 170 may be disposed at intervals on the second section 122 in the direction of extension of the second section 122. More sub-electrodes 170 mean higher electrode density, which is conducive to high-density mapping of the electrode and to collection of physiological signals from the predetermined site.

Preferably, each of the first section 121 and the second section 122 is provided thereon with some of the sub-electrodes 170. This allows for an increased ablation depth and improved accuracy of high-density mapping. The base 160 has a planar strip-like (i.e., elongate and rectangular) shape. The sub-electrodes 170 on the first section 121 and the sub-electrodes 170 on the second section 122 are arranged on opposing sides of the base 160. In one exemplary embodiment, in the contracted configuration, the base 160 is perpendicular to the radial direction of the catheter 200, with the sub-electrodes 170 on the first section 121 being located on an inner surface of the base 160, and with the sub-electrodes 170 on the second section 122 being located on an outer surface of the base 160. In this case, when the main electrode portion 120 is in the folded configuration, all the sub-electrodes 170 are oriented distally. In an alternative embodiment, the sub-electrodes 170 on the first section 121 are disposed on the outer surface of the base 160, while the sub-electrodes 170 on the second section 122 are disposed on the inner surface of the base 160. In this case, when the main electrode portion 120 is in the folded configuration, all the sub-electrodes 170 are oriented proximally. Here, the inner surface of the base 160 refers to the surface of the base 160 closer to the catheter 200, while the outer surface of the base 160 refers to the surface of the base 160 farther away from the catheter 200. Those skilled in the art may appropriately arrange the sub-electrodes 170 on the outer surface and/or the inner surface of the base 160 according to the location of the predetermined site in the patient's body.

The present invention is not limited to the base 160 being perpendicular to the radial direction of the catheter in the contracted configuration, because in some alternative embodiments, it may form an angle with the catheter (which may be 0°, corresponding to perpendicularity of the base 160 to the radial direction of the catheter). The angle may be arbitrary, as long as the opposite surfaces of the base 160 are respectively oriented proximally and distally.

Further, at least some of the sub-electrodes 170 may have different radial dimensions. This may be interpreted as at least some of the sub-electrodes 170 optionally having different cross-sectional areas. One or more sub-electrodes 170 around the middle of the first section 121 may have a greater radial dimension than the sub-electrodes 170 located around the opposite ends of the first section 121, and/or one or more sub-electrodes 170 around the middle of the second section 122 may have a greater radial dimension than the sub-electrodes 170 located around the opposite ends of the second section 122. FIGS. 7 and 8 show a specific example in which the first section 121 and the second section 122 are curved. In this example, for the first section 121 and/or the second section 122, one or more middle sub-electrodes 170 have the greatest radial dimension, and the other sub-electrodes 170 have their radial dimension decreasing toward the opposite sides. Due to the folded configuration of the main electrode portion 120, there is a larger spacing between the middle portions of the first section 121 and the second section 122, the sub-electrodes 170 with larger radial dimensions can be arranged, and there is a smaller spacings between the end portions of the first section 121 and the second section 122, the sub-electrodes 170 with smaller radial dimensions can be arranged. As a result, this design allows an optimized arrangement of sub-electrodes 170 and maximizes utilization of redundant space, a larger area of the electrode can be used for ablation and more concentrated ablation energy can be delivered.

Preferably, the radial dimension of the sub-electrodes 170 on the first section 121 gradually decreases from the middle of the first section 121 to its opposing ends, and/or the radial dimension of the sub-electrodes on the second section 122 gradually decreases from the middle of the second section 122 to its opposing ends. This allows an even better arrangement of sub-electrodes. With continued reference to FIGS. 7 and 8, in conjunction with FIG. 9, at least one of the first section 121 and the second section 122 may be curved, for example. When one of the first section 121 and the second section 122 is curved and the other is straight, in the folded configuration of the main electrode portion 120, the first section 121 and the second section 122 may generally define a substantially semi-elliptical shape (including a semi-circular shape). When the curvature of the curve is close to that of an elliptic curve, the semi-ellipse will be symmetric with respect to both its long and short axes. In this case, for each of the first section 121 and the second section 122, the radial dimension of the sub-electrodes thereon may gradually decrease from its middle to the opposing side (from one sub-electrode to another). Similarly, when the first section 121 and the second section 122 are both curved and the curvatures of their curves are close to those of elliptic curves, in the folded configuration, the first section 121 and the second section 122 may overall define an elliptic shape (including a circular shape). In this case, for each of the first section and the second section, the radial dimension of the sub-electrodes thereon may gradually decrease from its middle to the opposing side (from one sub-electrode to another). It would be appreciated that, in both the above "elliptic" and "semi-elliptical" examples, any pair of sub-electrodes 170 respectively on the first section 121 and the second section 122, which are symmetrical with each other with respect to the short axis (substantially symmetrical, and will be considered as being symmetrical even if there is an insignificant offset), may have either the same radial dimension or different radial dimensions, without departing from the scope of the present invention. Further, the above "elliptic" and "semi-elliptical" examples are presented merely for the purpose of illustration and are not intended to limit the invention in any way.

Preferably, the sub-electrodes 170 are raised over a surface of the base 160 and thereby can more easily come into contact with the predetermined site, leading to better ablation performance, when compared to the conventional electrode rings. Moreover, this can avoid contact of the base 160 with the predetermined site and reduce compressive stress imparted on the predetermined site (e.g., a pulmonary vein), allowing normal blood flow in the pulmonary vein and reducing thermal influence on ablation.

Optionally, the electrode may further include the transmission line 180, the sub-electrodes 170 are electrically connected to the transmission line 180. The transmission line 180 is used for transmission of energy to the sub-electrodes 170. The transmission line 180 may be made of copper, gold or another material. The transmission line 180 is covered with an insulating layer 190, which can insulate the sub-electrodes 170 from one another.

Preferably, each sub-electrode 70 has a flange. While the present invention is not limited to any particular direction of extension of the flange, it is preferred to extend toward the transmission line 180. The flange is covered with a layer and thereby secured to the transmission line 180. In this way, the sub-electrodes 170 can be kept stationary with respect to the transmission line 180. This fixation design can prevent falling of the sub-electrodes 170 and enable safer use. In particular, each sub-electrode 170 may have both a proximal flange and a distal flange so that it has a cross-sectional shape resembling the letter "Ω", wherein the flanges correspond to the horizontal bars of the letter. Optionally, the layer may be made of polyimide or liquid-crystal polymer (LCP).

Based on the electrode as defined above, the present invention also provides an electrophysiology catheter 200 including the above-discussed catheter 200 and electrode 100. At least one of the proximal electrode portion 110 and the distal electrode portion 130 of the electrode 100 is movably connected to the catheter 200, and the main electrode portion 120 of the electrode 100 can switch between the aforementioned contracted and folded configurations along with relative movement of the proximal electrode portion 110 and the distal electrode portion 130 along the catheter 200.

The electrophysiology catheter 200 may include a plurality of such electrodes 100, the plurality of electrodes 100 are arranged circumferentially around the catheter 200, preferably, the plurality of electrodes are arranged circumferentially around the catheter 200 in an even manner. This optimized arrangement allows a uniform distribution of ablation energy. Referring to FIG. 5, when the main electrode portions 120 of the electrodes are in the folded configuration, they overall substantially resemble petals, which can be brought into contact with the orifice of a pulmonary vein (which is substantially tapered in shape) to perform ablation and collect physiological signals.

Each electrode includes a plurality of sub-electrodes 170, the sub-electrodes 170 are scattered in intervals along the axis of the catheter 200 into a sub-electrode group. When the main electrode portions 120 of the electrodes 100 are in the contracted configuration, the sub-electrode groups of each adjacent pair of the electrodes 100 are staggered in the axial direction of the catheter 200. More specifically, for each adjacent pair of the electrodes 100, when in the contracted configuration, between projections of each adjacent pair of the sub-electrodes 170 in one of the electrode on the catheter is interposed a projection of one sub-electrode 170 in a second electrode. This space-saving design enables more electrodes 100 to be arranged on the catheter 200, which can lead to an increased ablation depth and hence allow the formation of a more extensive ablation lesion.

In an embodiment, the catheter 200 includes the outer tube 210 and the support shaft 220 movably inserted in the outer tube 210. In one preferred implementation, the proximal electrode portions 110 of the electrodes 100 are provided on the outer tube 210, and the distal electrode portions 130 of the electrodes 100 are provided on the support shaft 220. The support shaft 220 can be moved in the outer tube 210 to change the shape of the main electrode portions 120. Moreover, the support shaft 220 may have wire channels (not shown) axial extending therethrough, in which the traction wires (not shown) tied to the proximal electrode portions 110 and for guiding the electrodes to the predetermined site can be received. Preferably, the support shaft 220 is made of stainless steel or a reinforced plastic tube, and the wire channels are made of polytrafluoroethylene (PTFE) or high-density polyethylene (HDPE). Further, the channel may be internally coated with a hydrophilic or hydrophobic super-smooth layer.

Based on the electrophysiology catheter 200 as defined above, the present invention also provides an ablation system including the electrophysiology catheter 200. It would be appreciated that since the ablation system includes the electrophysiology catheter 200, it also provides all the benefits of the electrophysiology catheter 200. Operation and other necessary components of the ablation system will not be described in detail herein, and those skilled in the art can appropriately configure them as actually needed. For example, the ablation system may further include a control handle (not shown), which is coupled to the outer tube 210 so as to be able to drive the outer tube 210 to move to cause relative movement of the support shaft 220 and the outer tube 210 and hence change the shape of the main electrode portion 120. The ablation system may further include an energy supply platform, which is electrically connected to the electrodes 1 (more precisely, the sub-electrodes 170) and configured to supply them with energy (e.g., in the form of radio-frequency radiation, pulses or ultrasound waves)

required for ablation at the predetermined site. The ablation system may further include a temperature sensor and/or a pressure sensor. The temperature sensor may be used to detect a thermal effect during ablation, and the pressure sensor may be used to detect contact of the electrodes with the predetermined site.

In summary, the present invention provides an electrode, which is adapted to be disposed at a distal end of a catheter and includes a proximal electrode portion, a main electrode portion and a distal electrode portion, which are sequentially joined together from a proximal end to a distal end of the electrode. The main electrode portion includes a first section and a second section, which are joined to each other in an axial direction of the catheter 200. At least one of the proximal electrode portion and the distal electrode portion is movably connected to the catheter, and the main electrode portion is configured to switch between a contracted configuration and a folded configuration along with relative movement of the proximal electrode portion and the distal electrode portion along the catheter. When in the contracted configuration, the main electrode portion fits at its inner side over the catheter radially with respect thereto. When in the folded configuration, the main electrode portion is radially expanded outward with respect to the catheter so that the first section and the second section are inclined relative to each other and staggered transversely with respect to the catheter. Inclining and staggering the first section and the second section relative to each other as a result of radial expansion of the main electrode portion, instead of by twisting the electrode, can avoid a reduced contact area, or even increase the contact area, between the main electrode portion and a predetermined site. This can improve an electric field present around the predetermined site and enhance ablation performance.

The description presented above is merely that of a few preferred embodiments of the present invention and is not intended to limit the scope thereof in any sense. Any and all changes and modifications made by those of ordinary skill in the art based on the above teachings fall within the scope as defined in the appended claims.

What is claimed is:

1. An electrode configured to be disposed at a distal end of a catheter and used to transmit energy between a device and a predetermined site, the electrode comprising a proximal electrode portion, a main electrode portion and a distal electrode portion, which are sequentially joined together from a proximal end to a distal end of the electrode, the main electrode portion comprising a first section and a second section, which are joined to each other along an axis of the catheter, at least one of the proximal electrode portion and the distal electrode portion configured to be movably connected to the catheter, the main electrode portion configured to switch between a contracted configuration and a folded configuration along with relative movement of the proximal electrode portion and the distal electrode portion along the catheter, when the main electrode portion is in the contracted configuration, the main electrode portion inwardly abutting on the catheter along a radial direction of the catheter, when the main electrode portion is in the folded configuration, the main electrode portion expanding outward along the radial direction of the catheter so that the first section and the second section are inclined relative to each other to form a staggered arrangement along a transverse direction of the catheter, the electrode further comprising a base and a plurality of sub-electrodes, the plurality of sub-electrodes are disposed on the base and wherein the configuration is selected from the group consisting of:

(i) the plurality of sub-electrodes are provided on the first section at intervals in an extending direction of the first section, any of the sub-electrodes closer to the middle of the first section has a greater radial dimension than any of the sub-electrodes closer to either end of the first section; and (ii) the plurality of sub-electrodes are disposed on the second section at intervals in an extending direction of the second section, any of the sub-electrodes closer to the middle of the second section has a greater radial dimension than any of the sub-electrodes closer to either end of the second section.

2. The electrode according to claim 1, wherein the main electrode portion further comprises a folding portion, the folding portion joined to both the first section and the second section, wherein when the main electrode portion is in the folded configuration, the first section and the second section are folded and staggered through the folding portion.

3. The electrode according to claim 2, wherein the folding portion defines a groove, when the main electrode portion is in the folded configuration, the groove is configured to receive the first section or the second section.

4. The electrode according to claim 2, wherein the main electrode portion is configured to switch between the contracted configuration and an intermediate configuration and between the intermediate configuration and the folded configuration, wherein when the main electrode portion is in the intermediate configuration, a projection of the folding portion on the catheter is located between the proximal electrode portion and the distal electrode portion.

5. The electrode according to claim 4, wherein when the main electrode portion is in the contracted configuration or the intermediate configuration, the first section and the second section are staggered along the transverse direction of the catheter.

6. The electrode according to claim 1, further comprising a proximal mounting portion and a distal mounting portion, the proximal mounting portion and the distal mounting portion both parallel to the axis of the catheter, the proximal mounting portion configured to connect to the catheter through the proximal electrode portion, the distal mounting portion configured to connect to the catheter through the distal electrode portion.

7. The electrode according to claim 1, wherein at least one of the first section and the second section is curved or a polyline; or wherein the first section and the second section are both curved or polylines, and wherein the first section and the second section are curved toward opposite directions along the transverse direction of the catheter.

8. The electrode according to claim 1, wherein the radial dimension of the sub-electrodes on the first section gradually decreases from the middle of the first section to opposing ends thereof.

9. The electrode according to claim 1, wherein the sub-electrode protrudes from a surface of the base and configured to be brought into contact with the predetermined site.

10. The electrode according to claim 1, further comprising a transmission line, the plurality of sub-electrodes are electrically connected to the transmission line, and the transmission line is provided with an insulating layer for insulating the plurality of sub-electrodes from one another.

11. The electrode according to claim 1, wherein the base is embedded therein with an elastic nickel alloy.

12. An electrophysiology catheter, comprising a catheter and the electrode according to claim 1, wherein at least one of the proximal electrode portion and the distal electrode portion of the electrode is movably connected to the catheter, and the main electrode portion of the electrode is configured to switch between the contracted and folded configurations along with relative movement of the proximal electrode portion and the distal electrode portion along the catheter.

13. The electrophysiology catheter according to claim 12, comprising the plurality of electrodes, wherein the plurality of electrodes are arranged circumferentially around the catheter.

14. The electrophysiology catheter according to claim 13, wherein the plurality of the electrodes are uniformly arranged circumferentially around the catheter.

15. The electrophysiology catheter according to claim 12, wherein the catheter comprises an outer tube and a support shaft, the support shaft movably inserted within the outer tube, wherein at least one proximal electrode portion of the electrode is provided on the outer tube, and at least one distal electrode portion of the electrode is provided on the support shaft.

16. An ablation system, comprising the electrophysiology catheter according to claim 12.

17. The electrode according to claim 1, wherein the radial dimension of the sub-electrodes on the second section gradually decreases from the middle of the second section to opposing ends thereof.

18. The electrode according to claim 1, wherein the electrode further comprises a transmission line, the sub-electrode is electrically connected to the transmission line, wherein the sub-electrode has a flange which is covered by a layer and thereby secured to the transmission line, thereby limiting the sub-electrode in position on the transmission line.

19. The electrode according to claim 1, wherein the base is strip-like, wherein the sub-electrodes are provided on both the first section and the second section, and the sub-electrodes on the first section and those on the second section are positioned on opposite sides of the base.

20. The electrode according to claim 13, wherein each of the electrodes comprises a plurality of sub-electrodes, the plurality of sub-electrodes are arranged at intervals along the axis of the catheter to form a sub-electrode group, when the main electrode portions of the electrodes are in the contracted configuration, the sub-electrode groups of each adjacent pair of the electrodes are staggered along the axis of the catheter.

* * * * *